United States Patent
Lear et al.

(10) Patent No.: US 9,176,059 B2
(45) Date of Patent: Nov. 3, 2015

(54) OPTICAL ANALYTE SENSOR

(71) Applicant: Colorado State University Research Foundation, Fort Collins, CO (US)

(72) Inventors: Kevin L. Lear, Fort Collins, CO (US); David S. Dandy, Fort Collins, CO (US); Matthew D. Stephens, Fort Collins, CO (US); Guangwei Yuan, Fort Collins, CO (US)

(73) Assignee: COLORADO STATE UNIVERSITY RESEARCH FOUNDATION, Fort Collins, CO (US)

( * ) Notice: Subject to any disclaimer, the term of this patent is extended or adjusted under 35 U.S.C. 154(b) by 418 days.

(21) Appl. No.: 13/712,425

(22) Filed: Dec. 12, 2012

(65) Prior Publication Data

US 2013/0102090 A1    Apr. 25, 2013

Related U.S. Application Data

(62) Division of application No. 11/403,546, filed on Apr. 12, 2006, now Pat. No. 8,349,605.

(60) Provisional application No. 60/670,939, filed on Apr. 12, 2005.

(51) Int. Cl.
*G01N 21/00*    (2006.01)
*G01N 21/552*    (2014.01)
*G01N 33/543*    (2006.01)

(52) U.S. Cl.
CPC ........ *G01N 21/552* (2013.01); *G01N 33/54373* (2013.01)

(58) Field of Classification Search
None
See application file for complete search history.

(56) References Cited

U.S. PATENT DOCUMENTS

| 5,144,690 A | 9/1992 | Domash |
| 6,801,677 B1 | 10/2004 | Grace et al. |
| 2003/0132406 A1 | 7/2003 | Waldhausl et al. |
| 2005/0088648 A1 | 4/2005 | Grace et al. |

OTHER PUBLICATIONS

J.E. Midwinter, "On the Use of Optical Waveguide Techniques for Internal Reflection Spectroscopy," IEEE Journal of Quantum Electronics, vol. QE-7, pp. 339-344 (Jul. 1971), US.

N. Morita, A Rigorous Analytical Solution to Abrupt Dielectric Waveguide Discontinuities, IEEE Transactions on Microwave Theory and Techniques, vol. 39, No. 8, pp. 1272-1278 (Aug. 1991), US.

Chris Rowe Taitt, et al., Evanescent wave flourescence biosensors, Biosensors and Bioelectronics 20, 2470-2487 (Dec. 8, 2004) US.

Guangwei Yuan, et al., "Novel local evanescent field detection waveguide multianalyte biosensor," Optical Information Systems II, Proceedings of SPIE vol. 5557 (Oct. 2004) pp. 139-146, US.

*Primary Examiner* — Chris L Chin
(74) *Attorney, Agent, or Firm* — Samuel M. Freund; Cochran Freund & Young LLC

(57) ABSTRACT

A waveguide sensor capable of direct, real-time detection and monitoring of analytes in the vicinity of the waveguide surface without requiring the tagging or labeling of the analyte, is described. Analytic and numerical calculations have predicted that by locally detecting either changes in the evanescent field or changes in the light coupled out of the waveguide as a result of the presence of the analyte, high detection sensitivity will be able to be achieved.

10 Claims, 6 Drawing Sheets

OPTICAL ANALYTE SENSOR

RELATED CASES

The present application is a divisional application of U.S. patent application Ser. No. 11/403,546 filed Apr. 12, 2006, which claims the benefit of provisional patent application Ser. No. 60/670,939 for "Multi-Analyte Optical Sensor" by Kevin L. Lear et al., filed on Apr. 12, 2005, which application is hereby incorporated by reference herein for all that it discloses and teaches.

STATEMENT REGARDING FEDERAL RIGHTS

This invention was made with government support under Grant No. EB 00726 awarded by the U.S. National Institutes of Health to Colorado State University. The government has certain rights in the invention.

FIELD OF THE INVENTION

The present invention relates generally to analyte detection and, more particularly, to the use of evanescent and coupled electromagnetic waves from optical waveguide structures for sensing analytes.

BACKGROUND OF THE INVENTION

The low absorption loss, high sensitivity, and flexible light detection abilities of integrated optical waveguide analyte sensors make them suitable for many practical biological and chemical environments. Such analyte sensors include attenuation total reflection (ATR) [See, e.g., J. E. Midwinter in "On the use of optical waveguide techniques for internal reflection spectroscopy," IEEE J. Quantum Electron. 7, pp. 339-344 (1971)], Raman scattering waveguide (RSW) [See, e.g., Y. Levy et al. in "Raman scattering of thin films as a waveguide," Opt Commun. 11, pp.66-69 (1974)], and florescence spectrometry [See, e.g., W. M. Reichert et al. in "Excitation of fluorescent emission from solutions at the surface of polymer thin-film waveguides: an integrated optics technique for the sensing of fluorescence at the polymer/solution interface," Appl. Spectrosc. 41, pp. 636-640 (1987); U.S. Patent Application Publication No. US2006/0019244, Jan. 26, 2006 for "Planar Optical Waveguide Based Sandwich Assay Sensors And Processes for The Detection Of Biological Targets Including Protein Markers, Pathogens And Cellular Debris"; and U.S. Patent Application Publication No. US 2003/0132406, Jul. 17, 2003 for "Sensor Element For Optically Detecting Chemical Or Biochemical Analytes."].

Analytes are substances or chemical constituents undergoing analysis. Florescence-based waveguide analyte sensors rely on the use of excitation of a tag or label, such as a fluorescent dye, by excitation light guided in the waveguide with subsequent detection of florescence at a wavelength different from the wavelength of the excitation. Analytes may be dissolved in appropriate solvents therefore or may be suspended in fluids.

Present non-florescence-based optical waveguide analyte sensors rely on the optical properties of an analyte, such as refractive index or absorption, to alter the phase or amplitude of the light propagating in the waveguide. Included are an optical waveguide core; an optical waveguide lower cladding having a refractive index lower than that for the core; a photodetector; and optionally a substrate for additional mechanical support. Light is directed through the core, and evanescent portions of the optical field penetrate into regions near the core including the analyte and the lower cladding. The photodetector is positioned at the end of the waveguide to intercept the intensity of light traveling in the core which is responsive to changes in the evanescent field resulting from the interaction between the evanescent field and the analyte in contact with a portion of the exterior of the waveguide [See, e.g., U.S. Pat. No. 5,144,690 for "Optical Fiber Sensor With Localized Sensing Regions" which issued to Lawrence H. Domash on Sep. 1, 1992; and U.S. Pat. No. 5,991,479 for "Distributed Fiber Optic Sensors And Systems" which issued to Macros Y. Kleinerman on Nov. 23, 1999.].

Interferometric waveguide structures including Mach-Zehnder interferometers consisting of multiple waveguides that are coupled at two or more points along their lengths may be employed; however, a photodetector positioned at the terminus of one or more of the waveguides is used to detect the light propagated in the core. Light may be introduced into the waveguide using either end-fire, prism, or grating coupling techniques that are well known to those skilled in the art.

An alternative is to use a prism to permit the light to exit the waveguide away from the sensor region and direct the light coupled out through the prism to a detector. Such configurations permit only one analyte to be sensed with each waveguide.

Conventional ATR and RSW waveguide analyte sensors are often limited in the number of analytes that can be simultaneously detected by one sensor, and require complex sample preparation; that is, the large size and non-local detection characteristic of these sensors diminishes their applicability to complex and multiple analyte environments. Additionally, sensors using florescence spectrometry require that the target samples be prepared with chemically specific dyes or labels which increases the complexity and overall cost for analyses.

Accordingly, it is an object of the present invention to provide an apparatus and method for detecting analytes.

It is another object of the invention to provide an apparatus and method for simultaneously or individually detecting multiple analytes.

It is yet another object of the invention to provide and apparatus and method for detecting multiple analytes without requiring markers, such as fluorescent tags, attached to the analytes.

Additional objects, advantages and novel features of the invention will be set forth in part in the description that follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

The present invention overcomes the disadvantages and limitations of the prior art by allowing at least one light detector to be placed along the length of an optical waveguide, thereby permitting direct local detection of evanescent radiation emanating transversely from the waveguide core or light coupled out of the waveguide core into regions located alongside the waveguide responsive to analytes in the vicinity of the surface thereof, rather than directing the propagating field in the waveguide onto a detector disposed at the end of the waveguide. Hereinafter, optical guide, guide and waveguide are used interchangeably and may include optical waveguides, optical fibers, and the like, as examples. For bioassays, the analyte, also known as the target, may include antigens, single-strands of DNA (ssDNA), proteins, and the like as examples, and the probe species which is immobilized in the vicinity of at least one region of the surface of the optical waveguide, may include antibodies, complementary single-strands of DNA, aptamers, proteins, and the like, as examples, which may specifically bind to the probe species. More generally, analytes may include gases and liquids containing materials under investigation as solutes or as suspensions.

To achieve the foregoing and other objects, and in accordance with the purposes of the present invention, as embodied and broadly described herein, the analyte sensor or detector hereof includes in combination: a light source for generating light having a chosen wavelength or band of wavelengths; an optical guide having a surface and an axis, capable of receiving light from the light source and for transmitting the light along the axis, and having at least one region on the surface thereof wherein an evanescent field is generated substantially perpendicular to the axis of the guide such that the evanescent field extends from the surface within the at least one region; and at least one detector disposed in the vicinity of the at least one region where the evanescent field extends from the surface of the guide, for detecting the intensity of the evanescent field, whereby the analyte modifies the distribution of the evanescent field thereby changing the intensity thereof detected by the at least one detector.

In another aspect of the present invention, in accordance with its objects and purposes, the method for sensing or detecting an analyte hereof includes the steps of: introducing light having a chosen wavelength or band of wavelengths into an optical guide having a surface and an axis, capable of transmitting light along the axis, and having at least one region on the surface thereof wherein an evanescent field is generated substantially perpendicular to the axis of the guide such that the evanescent field extends from the surface within the at least one region; contacting the analyte with the evanescent field extending from the at least one region, whereby the analyte modifies the distribution of the evanescent field thereby changing the intensity thereof; and detecting the change of intensity of the evanescent field extending from the surface in the vicinity of the at least one region.

In yet another aspect of the present invention, in accordance with its objects and purposes, the analyte sensor or detector hereof includes in combination: a light source for generating light having a chosen wavelength or band of wavelengths; an optical guide having a surface and an axis, capable of receiving light from the light source and for transmitting the light along the axis, and having at least one region on the surface thereof wherein the index of refraction in the vicinity of the surface is modified by the presence of the analyte, and the intensity of light coupled out of the optical guide is changed; and at least one detector disposed on the side of the guide in the vicinity of the at least one region from which the light is coupled out of the optical guide, for detecting the change in intensity of the light coupled out of the optical guide at the chosen wavelength or band of wavelengths.

In still another aspect of the present invention, in accordance with its objects and purposes, the method for sensing or detecting an analyte hereof includes the steps of: introducing light having a chosen wavelength of band of wavelengths into an optical guide having a surface and an axis, capable of transmitting light along the axis, and having at least one region in the vicinity of the surface thereof wherein the refractive index thereof is altered by the presence of the analyte; placing the analyte in the vicinity of the at least one region of the surface, whereby the intensity of light coupled out of the optical guide is changed as a result of the presence of the analyte; and detecting the change of intensity of the light coupled out of the guide at the chosen wavelength or band of wavelengths in the vicinity of the at least one region.

Benefits and advantages of the present invention include, but are not limited to, the capability of simultaneous detection of multiple analytes without requiring fluorescent or other marker labeling using a waveguide sensor having a thin core region that creates a sufficiently large evanescent field capable of interacting with multiple adlayer regions which interaction can be locally detected near the sites of the adlayers. Detection of multiple antigens or pathogens using a compact sensor permits the present sensor to be useful for complex medical, security, and environmental applications.

BRIEF DESCRIPTION OF THE DRAWINGS

The accompanying drawings, which are incorporated in and form a part of the specification, illustrate several embodiments of the present invention and, together with the description, serve to explain the principles of the invention. In the drawings:

FIG. 2A shows a theoretical depiction of the power in the evanescent field detected by a photodetector for a detection system having probe materials deposited onto the surface of the waveguide core illustrated in FIG. 1 hereof, but without a target bound to the probe, while

FIG. 8A is a schematic representation of a cross-sectional side view of an embodiment of the apparatus of the present invention illustrating multiple sensing locations for detecting a multiplicity of analytes, or making several measurements of the same analyte, that bind to corresponding recognition layers located on the surface of the waveguide, while

DETAILED DESCRIPTION OF THE INVENTION

Figure 1:
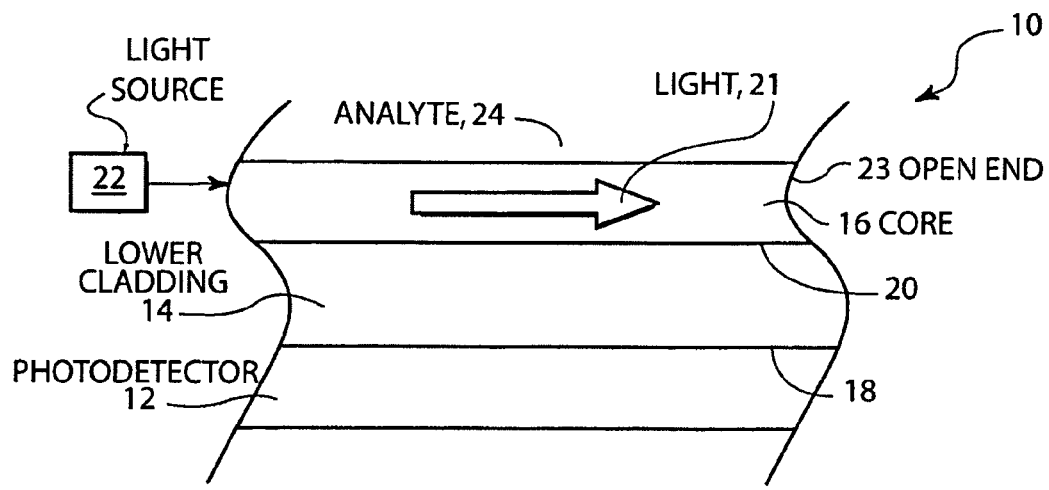
FIG. 1 is a schematic representation of a cross-sectional side view of one embodiment of the apparatus of the present invention illustrating the position of the photodetector relative to the core of the waveguide and the analyte.

Briefly, the present invention includes a waveguide sensor that for simultaneously detecting multiple analytes. The process of detection does not require labeling of the analytes with fluorescent or other tags. The waveguide has a thin core that can create large evanescent fields which can be detected in the region of the evanescent field and which fields interact with adlayer regions through which the evanescent fields pass, thereby generating changes in the field intensity.

In another embodiment of the invention, light may be coupled out of the waveguide in amounts which vary as a result of the interaction of the core with the analyte.

It has been theoretically determined by the present inventors that the power distribution of the electromagnetic field in the waveguide is dependent on the thickness of adlayers which are assumed, in the calculations which follow, to be target species bound to patches of probe species immobilized in the vicinity of the waveguide surface. To quantitatively calculate the detected power difference before and after the target/probe binding, waveguide parameters were investigated using the beam propagation method (BPM) and the finite difference time domain (FDTD) method electromagnetic field simulations.

Numerical modeling shows that high sensitivity can be achieved when a single mode asymmetric waveguide structure is operating near to the fundamental mode cutoff region. The cutoff region occurs where there are no longer any bound modes propagating with total internal reflection, and is a function of wavelength, layer dimensions (thickness), and the indices of refraction of the core and cladding layers. Cutoff is specific to the waveguide asymmetry, symmetric waveguides theoretically having no cutoff value. Although a waveguide does not need to be operated close to cutoff to function in accordance with the present invention, nor does it necessarily require asymmetry, the sensitivity to changes is maximized close to cutoff where a large evanescent field is generated and changes in adlayer thickness and width can strongly alter the electromagnetic field distribution. Such changes can be locally detected by an array of p-i-n (PIN), metal-semiconductor-metal (MSM), or other types of photodiodes in the lower cladding region, as an example. Near-field scanning optical microscopy (NSOM) has been used to detect the evanescent field in the upper cladding of the waveguide [See, e.g., Guangwei Yuan et al. in "Direct Imaging of Transient Interference in a Single-Mode Waveguide Using Near-Field Scanning Optical Microscopy," IEEE Photonics Tech. Lett. 17, pp. 2382-2385 (2005); and Guangwei Yuan et al. in "Initial Demonstration of a Local, Evanescent, Array Coupled Biosensor," $4^{th}$ IEEE International Conference on Sensors, paper B4P-G, Irvine, Calif., Oct. 31, 2005.]. Either detection method can be used to monitor the analyte binding in real time. In addition, the sensor of the present invention will be able to sense multiple regions of different antibody patches placed on the waveguide.

By treating the sensor structure as a number of abrupt adlayers on the surface of a waveguide which can be analyzed as corrugations or discontinuities, rigorous analytical solutions have been developed for mode coupling [See, e.g., A. Hardy, "Exact derivation of the coupling coefficient in corrugated waveguides with rectangular tooth shape," IEEE J. Quant. Electron., 20, pp. 1132-1139 (1984); and N. Morita, "A rigorous analytical solution to abrupt dielectric waveguide discontinuities", IEEE Trans. Microwave Theory and Tech. 39, pp. 1272-1278 (1991).]. The behavior of the electromagnetic field after an abrupt discontinuity has been derived by the present inventors using this approach and by using commercially available computer simulation tools including BPM and FDTD modeling of optical waveguide structures.

The intensity of evanescent fields decays exponentially in the transverse direction. In general, the evanescent field remains strong approximately 1 µm into gases having low indices of refraction or liquid analytes, and approximately 2 to 3 µm into higher index of refraction detectors. Therefore, although the extents of such fields are quite variable, they may be readily determined for various configurations of core and cladding thicknesses, core and cladding refractive indices, and wavelength using established methods known to those skilled in the art. In an embodiment of the present invention, the analyte may be bound to within about 100 nm of the optical waveguide, and the photodetector is placed within approximately 1 µm of the waveguide. A lower cladding was present in this embodiment.

Reference will now be made in detail to the present preferred embodiments of the present invention, examples of which are illustrated in the accompanying drawings. In what follows, identical callouts will be used to identify similar or identical structure. Turning now to FIG. 1, a schematic representation of a cross-sectional side view of one embodiment of the apparatus, 10, of the present invention is shown. Photodetector, 12, is located on the side of lower cladding layer, 14, away from core, 16, and has a surface, 18, substantially parallel to surface, 20, of core 16. Light, 21, having a chosen wavelength is directed into one end of core 16 using standard procedures, such as endfire coupling, prism coupling or grating coupling, as examples (not shown in FIG. 1) from light source, 22, and any remaining light which is either not absorbed or coupled out of core 16, exits through end, 23. Single mode and multimode lasers, light-emitting diodes, and other relatively narrow continuum light sources may be used, although single-mode lasers may be advantageous for endfire or higher grating coupling efficiency because of their better focusing characteristics. The intensity of guided light 22 is observable by photodetector 12, in accordance with the teachings of the present invention, as a result of the evanescent field associated with the optical field of the light transmitted through core 16 extending through lower cladding 14 into detector layer 12. Core layer 16 is chosen to have a larger refractive index than lower cladding 14. The field would typically be evanescent in lower cladding 14, but could become propagating in detector layer 12 if the refractive index of the detector layer is sufficiently high. This arrangement may also be considered to be evanescent coupling of the light in core 16 to a secondary lossy waveguide with the detector layer 12 serving as the core of the secondary lossy waveguide.

Another embodiment of detector layer 12 of the present invention is where the detector layer is disposed on the same side of core 16 as analyte 24. As an example, the detector may include a lower cladding 14, core 16, analyte 24, and detector layer 12, in that order. Other layers might be included intermediate to these layers so long as the evanescent field reaching the detector layer is sufficient to permit adequate detection of changes in the field distribution due to the presence or absence of adlayers formed on surfaces adjacent to the analyte region. Yet another embodiment would place detector layer 12 intermediate between core 16 and analyte 24. It is to be noted that placing detector 12 intermediate core 16 and analyte 24 requires that detector 12 is sufficiently thin such that the evanescent field can pass therethrough; however, for detectors disposed on the opposite side of core 16 from analyte 24, or where analyte 24 is disposed between core 16 and detector 12, either thick or thin detectors may be employed.

Thicknesses and materials of core 16 and lower cladding layer 14 are chosen such that a chosen amount of light coupling to photodetector layer 12 is generated relative to the optical properties of analyte, 24. Analyte 24 may be a gas, a liquid, a solution, or a porous solid that admits a gas or liquid. The analyte or changes in the analyte are detected by virtue of the changes in refractive index of the analyte either as a whole or in a portion of the analyte, in the region of the core. In the anti-guiding or leaky-mode operation of the optical waveguide, core layer 16 is chosen to have an index of refraction lower than that for analyte 24. In such a situation, light 22 is coupled into a propagating field in analyte 24 in an amount dependent upon the refractive index of the analyte. Higher analyte refractive indices decrease the amount of light coupled into the analyte for this anti-guiding configuration.

Core material 16 may also be chosen to have a higher refractive index than analyte 24. In this situation, only an evanescent portion of the optical field is present in the analyte; however, the refractive index of the analyte can alter the relative distribution of light between the propagating field 22 in waveguide core 16 and the evanescent field in lower cladding 14. An increase in the refractive index of the analyte increases the amount of evanescent field in the analyte and decreases the amount of evanescent field in the lower cladding and detector layers when positioned as shown in FIG. 1. As an example of a layer structure useful with an aqueous analyte 24 having an approximate refractive index of 1.33 is a silicon oxynitride core 16 having a refractive index ranging between 1.45 and 2.1, depending on its stoichiometry, and a silicon dioxide lower cladding having a refractive index of approximately 1.45. The core layer thickness can be between approximately 20 and 200 nm, with smaller values producing larger evanescent fields. The thickness of lower cladding 14 may be between approximately 100 and 2000 nm depending on the desired strength of field coupling to detector layer 12.

It should be mentioned that the waveguide core may have a rectangular, as described hereinabove, circular, as would be the situation for an optical fiber, elliptical, or other cross section. It may be advantageous to limit the lateral extent of the core layer so that the waveguide operates in a single transverse guided mode. The effective lateral index profile may be controlled by either completely or partially etching or otherwise changing the thickness of the high index of refraction core layer in regions outside the waveguide core. Waveguides having lateral definition are known as rib or ridge waveguides.

Detector layer 12 may be composed of a material that is absorbing at the wavelength of light guided in the waveguide. The wavelength of the light used can range from the ultraviolet through the visible to the infrared depending on the absorption properties of the detector. For example, silicon can be used as a detector element for wavelengths less than approximately 1100 nm. Other possible detector materials include, but are not limited to, direct-gap and indirect-gap inorganic and organic semiconductors in single crystal, polycrystalline, and amorphous forms. Other suitable photodetectors include photodiodes containing metal-semiconductor, p-n, or p-i-n junctions, photoconductors, and bolometers, as examples. Wavelengths generated by laser diodes at approximately 1550 nm, 1300 nm, 980 nm, 850 nm, 780 nm, 650 nm, and 400 nm, as examples, are convenient.

Many suitable detector materials 12, such as inorganic semiconductors, will have refractive indices greater than those of lower cladding 14 and often greater than that for core 16. In such situations, core layer 16 and detector layer 12 function as parallel waveguides that are evanescently coupled through lower cladding layer 14 although the absorbing detector waveguide would be considered lossy. The coupling coefficients between the two waveguides including the dependence on the refractive indices and thicknesses of core 16, lower cladding 14, and detector 12 layers can be calculated to determine the amount of power coupled into the detector layer. As stated hereinabove, analytical approximations may be employed to provide a rough calculation of the coupling coefficients following methods presented in textbooks on optical waveguides such as L. Coldren and S. Corzine [See, e.g., *Diode Lasers and Photonic Integrated Circuits*, New York, Wiley (1995), and the references cited therein.]. More complete or accurate results for coupling power into the detector layers 12 may be obtained from numerical simulations including those performed using commercial optical waveguide modeling software available from vendors including RSoft. A substantial amount of power may be coupled into the working length of the detector including multiple segments in the case that the detector is segmented as described hereinbelow. It may be advantageous to control the amount of power coupled to the detectors so that the tradeoff is appropriately balanced between providing sufficient signal to the detector and maintaining sufficiently low loss in the waveguide to permit the mode to propagate through a large number of detection regions. The amount of coupling for a particular core, cladding and detector layer design parameters may be usefully quantified in terms of the absorption loss, $\alpha$, in units of cm$^{-1}$. If the combined length of the detectors along a waveguide segment is denoted as L, then a useful embodiment of the present invention would be given approximately by the condition $0.1 < \alpha L < 2$.

It should be mentioned that in the event that multiple analytes or more than one measurement of the same analyte are to be detected by optical analyte sensor 10, detector 12 is better segmented by conductivity along the length of optical guide 16, than being segmented by refractive index. However, even for a detector having minor perturbations in its index of refraction, it is believed by the present inventors that there will be acceptable coupling to the waveguide.

In the situation where the refractive index of the core is greater than the refractive index of the analyte 24, lower cladding material 14 may be chosen to have an index of refraction higher than that of analyte 24, but lower than that of the core 16. This is a consequence of the rarity of materials having indices of refraction less than the index of refraction of water (<1.33). There is an advantage of using evanescence in the lower cladding to maintain the coupling to the detector layer sufficiently low that the bulk of the power is not significantly coupled into detector layer 12, as described hereinabove.

This asymmetric waveguide structure can be designed to operate near the cut-off by proper choice of the core thickness (between 10 and 500 nm) in order to enhance changes in the coupling to the detector as a result of small changes in the analyte's refractive index. As an example, such a structure will result when the analyte 24 is an aqueous solution having a refractive index of approximately 1.33, and the lower cladding 14 is silicon dioxide having a refractive index of 1.45. It has been determined by the present inventors that use of a core having dimensions of 100 nm thickness and 2 µm width (As an example, SiO$_x$N$_y$ having an refractive index of about 1.8, where the subscripts x and y indicate that the stoichiometry of the film may be adjusted to achieve the desired index of refraction.), and a 500 nm thickness for the SiO$_2$ lower cladding, that the guided mode is close to cutoff, with or without the presence of the adlayer, thereby providing better sensor response. It should be mentioned that if lower analyte detector sensitivity can be accepted, a 200 nm core thickness has advantages in manufacturing of the device. Reducing the thickness and decreasing the refractive index of core 16 both generally cause an asymmetric waveguide to be closer to cut-off. As such, there is a tradeoff between core thickness and refractive index when designing the waveguide to be close to cut-off. The choice of nominal core thickness and refractive index will be guided by the ability of manufacturing processes to control the thickness and material composition, including as appropriate the stoichiometry, of the core which in turn affects the refractive index of the core.

Figure 2A:
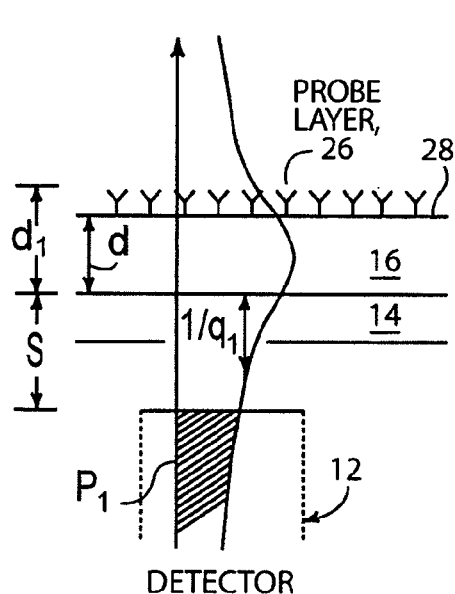

Turning to FIG. 2A and again to FIG. 1, it is assumed that analyte 24 is an aqueous analyte having a refractive index of $n_u=1.33$ that serves as the upper cladding of waveguide core 16. As stated hereinabove, materials for waveguide core 16 can be chosen within certain constraints to have an index $n_c$. Lower cladding 14 is chosen to have index $n_l$. In FIG. 2A, detector 12 is shown detached from surface 18 of lower cladding 14, by a distance, S. Shown also in FIG. 2A is probe layer, 26, immobilized on surface, 28, of core 16. The core thickness before binding is shown as $d_1$; after binding with target species, 30, in aqueous analyte 24, the core thickness becomes $d_2$ ($d_1$~110 nm, and 110 nm<$d_2$<200 nm have been simulated). Bare waveguide core 16 thickness is d, and any adlayer (target/probe layer), 32, thickness is $d_a$. The probe and/or target films generally have a refractive index $n_a=1.45$, since such films are principally proteins. When the target is bound, the field profile shifts such that there is less overlap with the detector. That is, target binding changes the evanescent decay constant from $q_1$ to $q_2$ (measured in cm$^{-1}$, as an example), with $q_2>q_1$. Values of $q_1$ and $q_2$ may be calculated from the details of the refractive indices of the layers including the adlayer, using well-known numerical procedures, such as those mentioned hereinabove.

In order to have only one bound mode, there is one unique solution for the propagation constant $\beta=k\cdot n_e$, where k is the free space wave vector and $n_e$ is effective refractive index. Other conditions such as $n_c>n_e>n_u$, $n_l$, are required. A large core thickness will make the waveguide multimode, whereas a small core thickness may make efficient light coupling more difficult. For purposes of illustration, the waveguide core thickness has been chosen to be 100 nm. Neglecting the longitudinal dependence, the transverse electromagnetic field profile of the $TE_0$ mode can be expressed as:

$$E'(x) = \begin{cases} A \cdot e^{-px}, & x < 0 \\ B \cdot f(x, \beta), & 0 \le x \le d \\ C \cdot e^{qx}, & d < x, \end{cases} \quad (1)$$

where $\beta$ is the propagation constant.

Figure 2B:
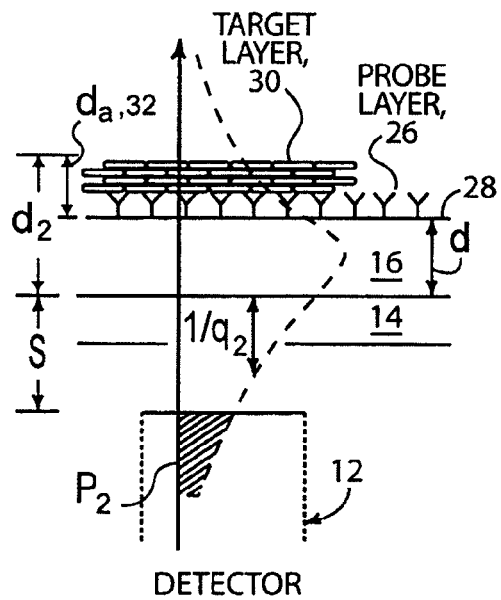
FIG. 2B is a depiction of the power in the evanescent field detected by the photodetector after the probe is exposed to the appropriate target-containing solution or suspension, respectively, and target binding takes place, the difference between the two detected power levels being responsive to the optical characteristics of the bound target layer.

The function, $f(x,\beta)$, is related to the geometry of the guided layer and must meet the boundary conditions. It is approximately sinusoidal for core layers having constant index of refraction. Other important parameters include the penetration depth $1/p=1/\sqrt{\beta^2-k^2 n_u^2}$ and $1/q=1/\sqrt{\beta^2-k^2 n_l^2}$ in the upper and lower cladding regions, respectively. Larger penetration depths result in more power being confined in the evanescent field. In FIG. 2A, $P_1$ denotes the detected power before the antigen-antibody binding, whereas $P_2$, in FIG. 2B denotes the detected power after the antigen-antibody binding. In order to find the relative power change, some approximations must be made. As described hereinabove, this system is an asymmetric waveguide operating near the fundamental mode cut-off region. The penetration depth in the lower cladding is much larger than that in the upper cladding region and the waveguide core thickness; that is, $1/q \gg 1/p \gg d$ for this configuration. Therefore, the normalized detected power difference can be approximately expressed as:

$$\Delta P/P_0 = \eta \cdot \frac{P_1-P_0}{P_1} \approx 1 - \frac{p_1}{p_2} e^{-2(q_1-q_2)(S-d/2)} \quad (2)$$

In Equation 2, $p_1$ and $p_2$ are associated with penetration depth in the upper cladding before and after binding, respectively. Similarly, $q_1$ and $q_2$ are associated with penetration depth in the lower cladding before and after binding, respectively. The mode coupling efficiency, $\eta$, is close to unity in most situations. However, in a rigorous derivation, $\eta$ may have a value less than unity. Since the sensor regions can be treated as waveguide corrugations or discontinuities, the theoretical methods in references [See, e.g., A. Hardy; and N. Morita, supra.] are valid for calculating $\eta$ general, the theoretically calculated $\eta$ is between 0.96 and 0.99, while the BPM simulated result $\eta$ is between 0.95 and 0.99.

The analytic calculations provide useful results for layers that are sufficiently long that transients induced by the edges have died out, and provide useful indication of trends for shorter layers, but may over predict the response. Numerical simulations are required to determine how rapidly the field adjusts after a step. Numerical simulations are generally more accurate and more tractable for complex structures, especially for actual 2-dimensional cross-sections of the cores.

BPM and FDTD codes from RSoft Design Group, Inc. were used for numerical simulations. The BPM algorithm is based on a finite difference beam propagation method. This computation technique uses finite difference methods to solve the parabolic or paraxial approximation of the Helmholtz equation. The FDTD algorithm is a more rigorous solution to Maxwell's equations and does not contain significant approximations or theoretical restrictions. This method is widely used as a propagation solution technique in integrated optics. Numerical simulations of the new sensor design have centered on waveguide structure optimization, sensitivity analysis, and surface scattering. In most of the calculations, both BPM and FDTD were employed.

Good sensitivity for the present apparatus requires an adequate detected power difference $\Delta P$ to provide sufficient signal-to-noise ratios. The power difference is usually normalized by $P_0$, which is taken as the detected power in the absence of any adlayer. Assuming the target adlayer thickness before binding is known, the adlayer thickness change after binding can be determined from $\Delta P/P_0$. Optimization of core and cladding refractive indices and detector-to-core distance will be discussed hereinbelow, as will corrections for finite length adlayers and signal-to-noise ratio (SNR).

Figure 3:
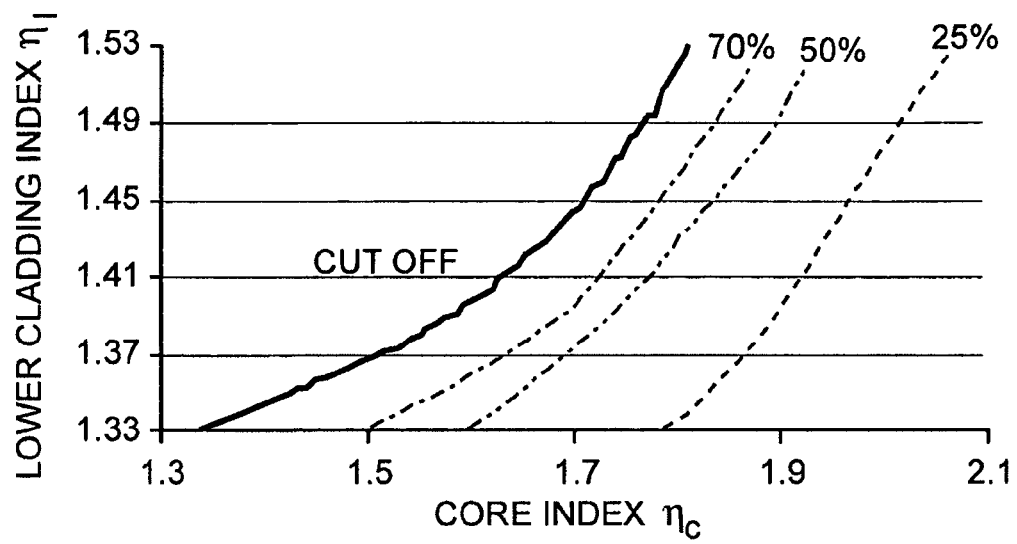
FIG. 3 is a graph of the theoretical contour plot of detected evanescent field power difference as a function of core and lower cladding refractive indices.

As stated hereinabove, the analyte solution serves as the upper cladding of the waveguide, but appropriate optical materials for core 16 and lower cladding 14 are now considered. This is a good assumption for thin antigen layers, before the completed antigen/antibody adlayer is formed. FIG. 3 is a contour map for $\Delta P/P_0$ as a function of core and lower cladding refractive indices. It is found that a large $\Delta P/P_0$ may be achieved near cut-off regions. Two waveguide structures have been investigated. The first is a symmetric waveguide, where the core is constructed from free-standing polyimide materials having $n_c=1.37$. In this situation, the upper and lower cladding are made of the aqueous analyte solutions having $n_u=1.33$. In such a structure $\Delta P/P_0=80\%$ may readily be obtained. But fabrication is likely to be difficult due to processing procedures necessary to obtain a 100 nm thick free-standing waveguide. For the second structure, an asymmetric waveguide, the core is made using $SiO_xN_y$, where the subscripts x and y indicate that the stoichiometry of the core may be adjusted to achieve n=1.8~2.1. Again, the upper cladding is the aqueous solution with $n_u=1.33$, but now the lower cladding is made of a solid material such as $SiO_2$ having $n_1=1.45$, as an example. It has been found that this waveguide would be easier to fabricate and still offer high sensitivity. In FIG. 3, the simulation was achieved with the assumption that the adlayer thickness changes in the amount of 100 nm, and the detector was placed at a distance S=1 μm from the waveguide core.

Figure 4:
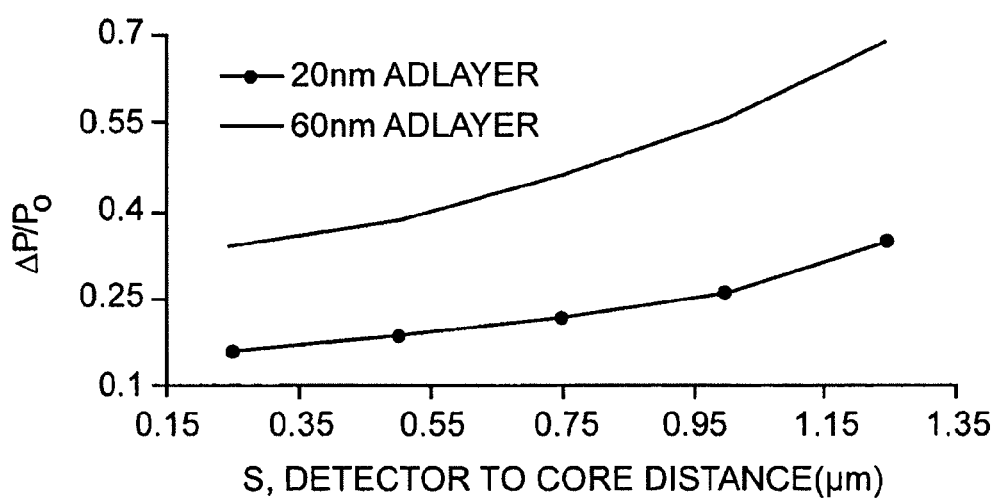
FIG. 4 is a graph of the theoretical normalized detected evanescent field power difference as a function of the distance between the core of the waveguide and the photodetector.

FIG. 4 shows the dependence of $\Delta P/P_0$ on detector-to-core distance, S. Two adlayer thickness values have been chosen: 20 nm and 60 nm. In both situations, $\Delta P/P_0$ changes exponentially with S which agrees with the Equation 2 hereof. The core index of refraction is 1.8 and the lower cladding index of refraction is 1.45. In general, larger detector-to-core distances result in a larger $\Delta P/P_0$. However, the absolute magnitude of $P_o$ decreases with larger detector-to-core distances.

Figure 5:
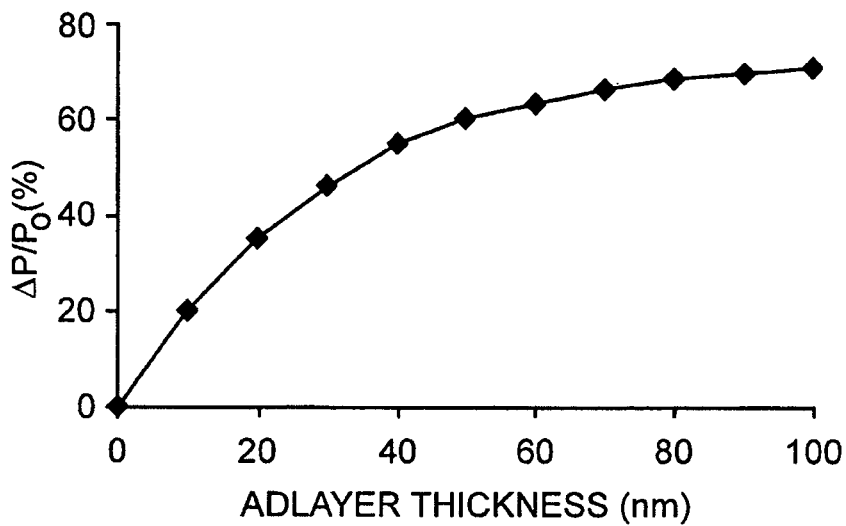
FIG. 5 is a graph of the theoretical normalized detected evanescent field power difference as a function of the thickness of the adlayer.

Assuming a detector-to-core distance S=1 μm, the dependence of $\Delta P/P_0$ on the adlayer thickness is shown in FIG. 5. The core index of refraction is assumed to be 1.8 and that for the lower cladding is 1.45.

Figure 6:
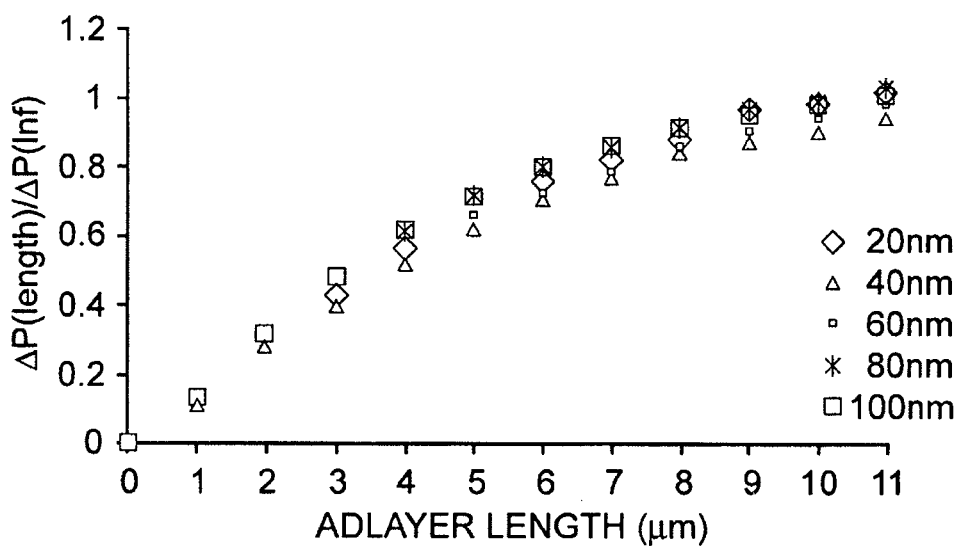
FIG. 6 is a graph of the ratio of theoretical detected evanescent field power for finite length evanescent field detector segments normalized by the theoretical detected evanescent field power for a semi-infinite detector as a function of adlayer length.

Although the sensitivity of the sensor for long adlayer patches is large, the sensitivity decreases when decreasing the length of the adlayer. For finite-length adlayers, the field does not respond rapidly to changes in the thickness. Two issues are addressed for finite-length adlayer detectors: (1) how the finite length adlayer affects the total sensitivity; and (2) how the field response to one adlayer affects the response to a separate adlayer region at another point on the waveguide. It has been determined that the ratio of $\Delta P(\text{length})/\Delta P(\text{Inf})$ is substantially independent of the adlayer thickness as may be observed from FIG. 6.

For multiple analyte sensors, numerical simulations have included interactions between neighboring sensing regions of the waveguide. Perturbations of the field distribution have been found to exist for some distance beyond the adlayer. The amplitude of the perturbation decays approximately exponentially with decay lengths on the order of 100 μm.

Figure 7:
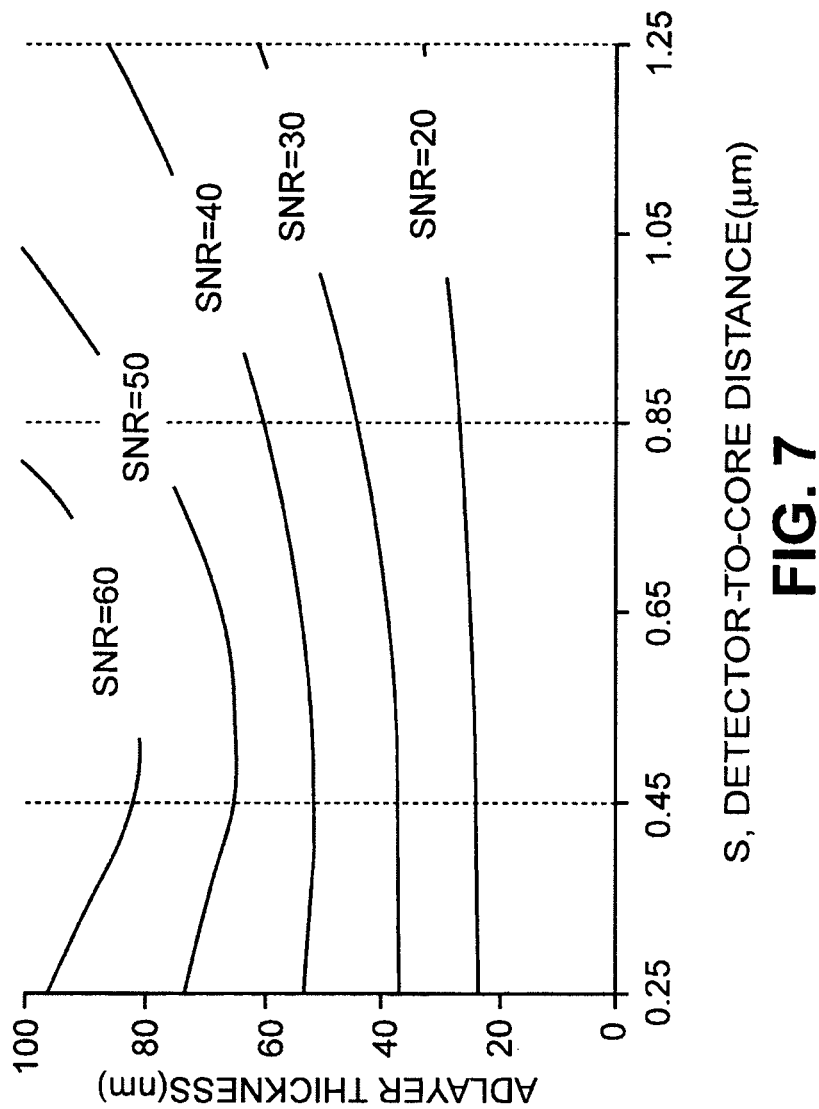
FIG. 7 is a graph of the theoretical signal-to-noise ratio for different adlayer thicknesses and detector-to-core distances.

Another source of noise is surface scattering. Shot noise and thermal noise in the waveguide can be decreased by using a filter to narrow the bandwidth, giving an signal-to-noise ratio (SNR) of the order of 120 dB. However, surface scattering as a noise source may be the limiting factor. A waveguide sample surface has been investigated using atomic force microscopy (AFM) imaging. The roughness of the $SiO_2$ substrate is Ra=0.4 nm~0.45 nm. The roughness of the core $SiO_xN_y$ film is Ra=0.65 nm~1.25 nm. An artificial roughness structure has been added onto the waveguide surface for simulations. SNR due to surface roughness is plotted in FIG. 7 in a contour plot as a function of detector-to-core distance, S, and adlayer thickness, $d_a$. Waveguide roughness should be minimized using suitable deposition procedures known in the art. Excessive roughness leads both to high loss in the waveguide and to the scattering of light into the detectors which are intended to receive evanescent light from the waveguide. It may be advantageous that the approximate roughness of the waveguide is less than the thickness of the adlayer to be detected, for example, less than 10% of this thickness.

A number of $SiO_xN_y$ films have been deposited on either $SiO_2$ or glass slips. Waveguides have been patterned via photolithography and dry etching. These waveguide samples are about ≤10 μm in width and approximately 100 nm in height. To obtain a large light coupling efficiency, the input end of the waveguide has been designed to have a tapered structure. Experimental work also has been undertaken on coupling light into waveguides. The relatively high refractive index of prototype $SiO_xN_y$ waveguide samples requires precisely controlled coupling methods. Both prism and end-fire coupling approaches have been employed. An apparatus including a 10 nm-step-resolution piezoelectric xyz translation stage has been assembled and is being used for coupling and positioning. End fire coupling for introducing light into the waveguide has been employed, where the aligned optical fiber is bonded to the core using epoxy. Fundamental-mode to higher-order mode interference has also been studied using NSOM which indicates that a single, guided mode gives rise to the best performance.

In summary, at present, changes in evanescence in waveguides ($SiO_xN_y$ core with $SiO_2$ lower cladding) have been measured using NSOM when layers having n~1.5, such as photoresist material, have been deposited on the waveguide surface. All other results herein presented are the product of simulations.

Figure 8A:
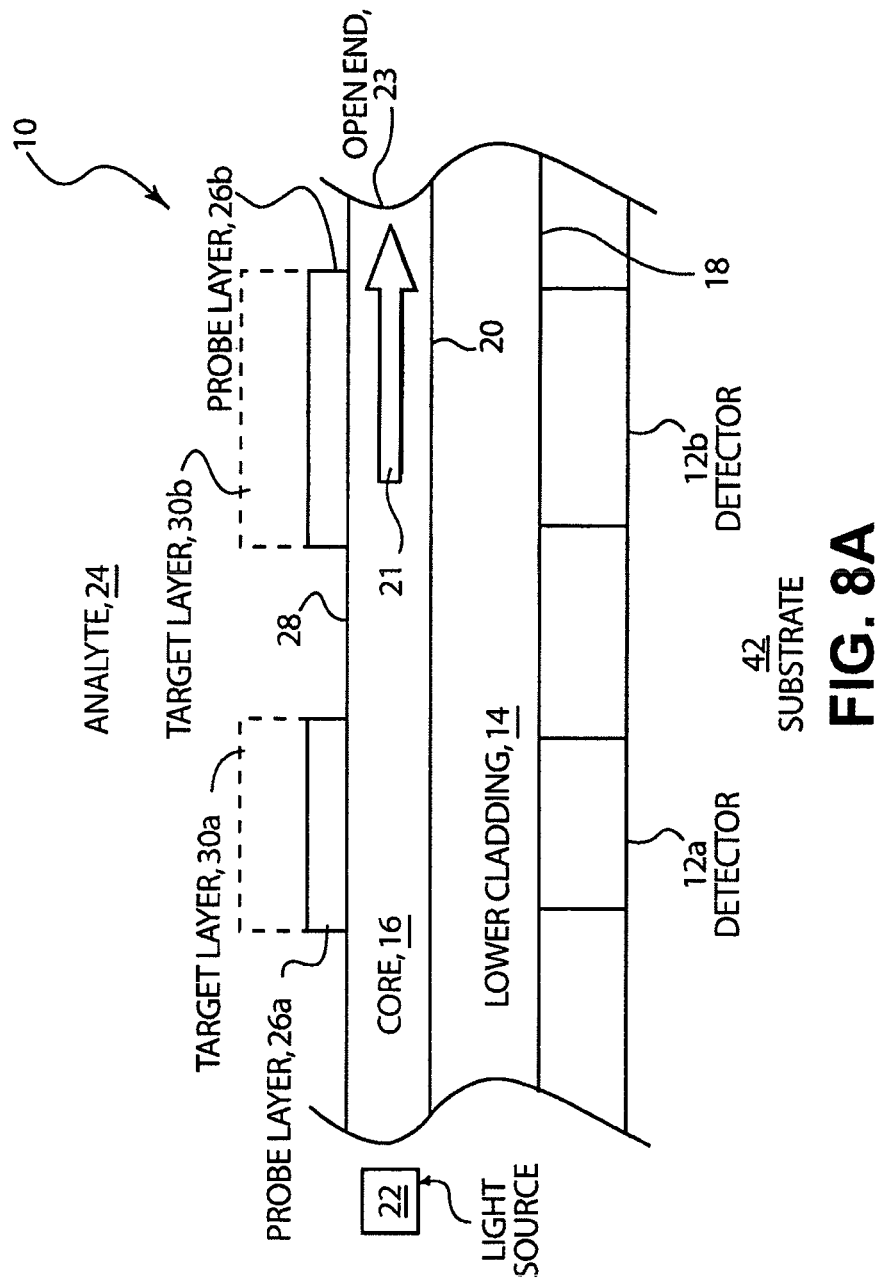
Figure 8B:
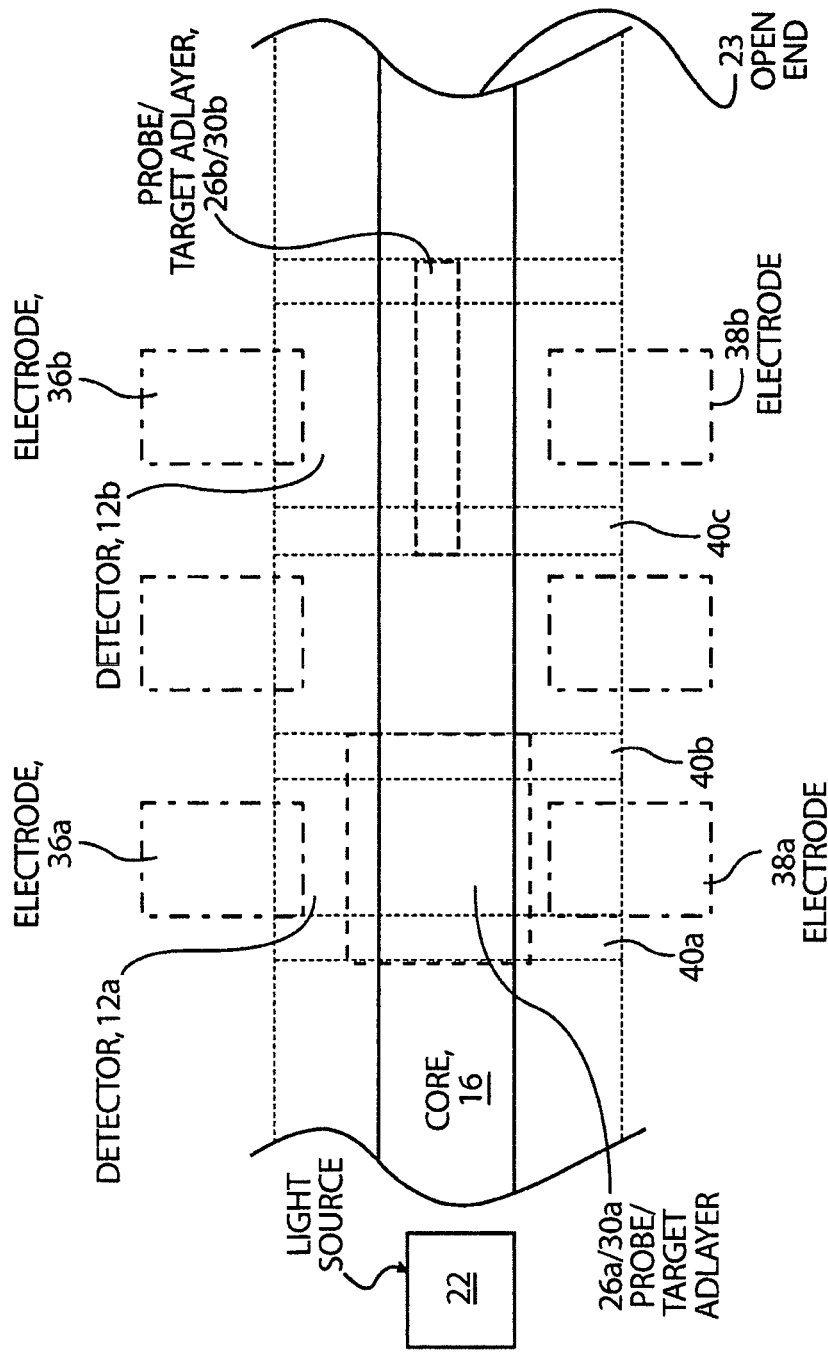
FIG. 8B is a schematic representation of a top view thereof.

FIG. 8A is a schematic representation of a cross-sectional side view of an embodiment of the apparatus of the present invention illustrating multiple sensing locations for detecting a multiplicity of different analytes that bind to corresponding recognition layers located on the surface of the waveguide, while FIG. 8B is a schematic representation of a top view thereof. The sensor may function by the formation of a single adlayer 26a/30a, or a multiplicity thereof identified as layers 26a/30a and 26b/30b in FIG. 8A, on or near waveguide core 16. Adlayer may consist of proteins or other organic molecules, inorganic particles, metals, combinations of these materials, and materials to be sensed might be carried to the surface of the waveguide by analyte 24 in liquid or vapor phase. The evanescent field distribution in the upper or lower cladding and thus the power coupling to detector layer 12, shown as a multiplicity of detectors, 12a, 12b, opposite corresponding adlayers 26a/30a and 26b/30b, are sensitive to the refractive index and thickness of their corresponding adlayers. The adlayer's refractive index may be higher, lower, or equal to the refractive index of the core. Additional thin layers may be interposed between the waveguide core and the adlayer so long as those layers permit substantial penetration of the optical field into the adlayer or analyte. Such layers may be useful, for example, for chemical isolation of the analyte from the core material, modifying the surface properties of the core layer, or providing chemical specificity.

Chemical specificity of particular adlayers can be provided by placing thin layers of chemical or molecular recognition materials (probe species) substantially on the waveguide core, as is illustrated by probe layers 26a and 26b, which may include DNA, RNA, antibodies, antigens, aptamers, or polymers, gels, or emulsions that react with specific sets of species to be recognized. The use of molecular recognition layers is known by those skilled in the art of immunoassay and affinity binding sensors.

FIG. 8A shows recognition (antibody probe) patches 26a and 26b immobilized on waveguide core 16 that can sequester specific target antigens, as an example, forming thereby layers 30a and 30b, respectively, if these species are present in analyte 24. Clearly, a greater number of probe patches can be employed depending on the purpose of the sensor. As an example of the target species specificity of the present sensor, if only species, 30a, which binds to molecular recognition layer 26a is present, then adlayer 32 would form at 26a/30a, but not at 26b/30b. Additionally, sensor 10 is very sensitive to the target analyte species, since probe layers 26a and 26b can be allowed to "develop" adlayer 32; that is, by permitting analyte 24, containing target species to be sensed, to remain in contact with probe layers 26a and 26b for a sufficient amount of time that a detectable quantity of target species is deposited, successful target monitoring or sensing can be achieved using the sensor of the present invention.

Recognition layers can be patterned in lateral extent, and multiples of such layers targeting different species can be position on the same waveguide core using photolithography, ablation, inkjet printing, scanning probe microscopy, imprint lithography, or other known methods for patterning recognition layers. Patterned recognition layers intended to detect one or more species may be positioned on the same waveguide. As stated hereinabove, when multiple recognition layer regions are present that need to be independently detected, the photodetector layer 12 may be segmented into regions that substantially correspond in extent along the length of the waveguide core 16 to the extent of the recognition regions. For example, photodetector segment 12*a* would provide a signal principally due to adlayer 26*a*/30*a* and photodetector segment 12*b* would provide a signal principally due to adlayer 26*b*/30*b*. Other segments of the photodetector, not shown in FIG. 8A, may not be used for sensing or may be used to provide reference signals where adlayers do not form. It may be advantageous to provide multiple detector segments in the vicinity of each recognition layer region in order to perform signal averaging or to determine the rate of change of the field, as examples.

FIG. 8B shows a top view of the structure illustrated in FIG. 8A. Electrodes 36*a* and 38*a* are attached to photodetector segment 12*a*, while electrodes 36*b* and 38*b* are attached to photodetector segment 12*b* in order to permit analyte measurements. Photocurrents or photovoltages are measured from these electrodes using conventional measurement apparatus, not shown in FIG. 8B. Such apparatus may include electronics formed on a common substrate with the photodetectors. Core 16 is shown to have a limited width whereby a single lateral mode is propagated; that is, in the plane of the wafer, but perpendicular to the direction of propagation. The photodetector segments extend to both sides of waveguide core 16. The recognition layer 26*a* and corresponding adlayer 30*a* regions may or may not be wider than the waveguide as shown in FIG. 8B for regions 30*a*/26*a* and 30*b*/26*b*, respectively.

The width of core layer 16 is defined by either completely removing the core layer in the regions alongside the core forming a rib waveguide or by partially etching them in order to form a ridge waveguide. The width and type of waveguide can be designed to be multimode or single-mode as understood by those skilled in the art of waveguide design. Electrodes, 36*a*, 38*a*, 36*b*, and 38*b* are separated from core 16 or fabricated from low-loss materials so as not to contribute excessive optical loss to the waveguide, while simultaneously offering acceptable electrical resistance so as not to substantially diminish the electrical signals from photodetectors 12*a* and 12*b*, respectively.

In one mode of operation, all of the electrodes on one side of the waveguide, for example, 36*a* and 36*b*, are biased with one polarity of voltage, and all of the electrodes on the opposite side, for example, 38*a* and 38*b*, are biased with the opposite polarity of voltage. In such situation, changes in an adlayer region modulate the optical power absorbed by the underlying photodetector segment and thus modulates the current flowing from or voltage developed by the corresponding electrodes. Since only the electrodes on one side the core are required to determine the amount of current flowing in the corresponding photodetector segments, all of the electrodes on the other side of the core may be electrically connected to a common circuit node to simplify the wiring. In one embodiment of the invention, the photodetector layer is a semiconductor so that the photodetector acts as a photodiode. In this situation, possible photodiode configurations include a metal-semiconductor-metal configuration using lightly doped or undoped semiconductor and a p-i-n configuration where the photodetector layer contains regions of p-type and n-type doping. Other configurations or photodiodes may also be used. If electrical isolation is required between the photodetector segments, insulating regions, 40*a*, 40*b*, and 40*c*, may be interposed between the photodetector segments, and substrate, 42, may be substantially insulating. Insulating regions 40*a*, 40*b*, and 40*c*, may be created by many methods known to those skilled in the art of photodetector array fabrication including, but not limited to, ion implantation and etching followed by refilling with an insulating material.

In actual operation, the majority of the light in the waveguide may be extinguished by the time it reaches the end of the waveguide. However, some light may escape from open end 25, and it may be desirable to recapture this escaped radiation to reduce the possibility of scattering back into the system when the apparatus 10 is placed in a solution containing analyte 24. It is not necessary for device operation that this is done, but it may be desirable to place reflection reducing materials, such as anti-reflection coatings, absorber layers, angled facets, waveguide bends, or other means known to those practiced in the art of waveguide engineering to reduce reflections at the end of the waveguide.

It is to be mentioned that multiple waveguides may be employed for analyte analysis. By use of waveguide splitters and bends, light from a single optical source can be transmitted to multiple, non-intersecting waveguide segments, each of which might contain multiple sensing regions. In this manner, additional sensor regions could be provided without significantly increasing the complexity of the light coupling. Moreover, the additional waveguide structures might be used for sensing additional analytes.

In "Direct Imaging of Transient Interference in a Single-Mode Waveguide Using Near-Field Scanning Optical Microscopy" by Guangwei Yuan, supra, it is stated that near-field scanning optical microscopy was used to image transient interference between the guided mode and a leaky mode induced in a single-mode waveguide due to a localized adlayer. Such interference may impact the element spacing for the sensors of the present invention and sufficient spacing between sensitization elements may allow such oscillations to decay. One may also attempt to minimize step heights associated with the sensitization layer in the absence of the analyte under investigation.

A longitudinal change of refractive index in isolated detectors below the waveguide is likely to have the same effect. Therefore, a continuous layer of photodetector material with many electrical contacts, all to the same piece of silicon or other detector material may generate improved performance for the light coupling embodiment of the present invention. Implants, diffusion, or other processes known to alter the conductivity between the elements of the continuous detector material may be useful to electrically isolate them from one another in some cases, but it is not clear that this is necessary. Such processes are expected to have only small effects on the refractive index properties of the material and could be engineered to trade off minimal disruption of the optical field with adequate isolation if any is required.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for detecting an analyte, comprising the steps of:
   providing an analyte sensor, comprising in combination:
   a light source for generating light having a chosen wavelength or band of wavelengths;
   an optical guide having a first surface and an axis, capable of receiving light from said light source and for guiding the light along the axis, and having at least one region on the first surface thereof wherein an evanescent field is generated substantially perpendicular to the axis of said guide such that the evanescent field extends from the first surface within the at least one region;
   at least one detector disposed in the vicinity of the at least one region of said guide and ≤45 μm from said guide, for detecting the intensity of the evanescent field; and
   a substrate not interposed between said optical guide and said at least one detector, for supporting said waveguide and said detector, whereby the analyte in the vicinity of the at least one region modifies the distribution of the evanescent field thereby changing the intensity thereof detected by said at least one detector;
   introducing light having a chosen wavelength or band of wavelengths into said optical guide;
   contacting the analyte with the evanescent field exiting the at least one region, whereby the analyte modifies the distribution of the evanescent field thereby changing the intensity thereof; and
   detecting the change of intensity of the evanescent field extending from the at least one region of the first surface in the vicinity of the at least one region to detect the presence of analyte.

2. The method of claim 1, wherein the optical guide guides a single mode of the light at close to cut-off independent of the presence of the analyte.

3. The method of claim 1, wherein the optical guide is substantially rectangular.

4. The method of claim 3, wherein the single mode comprises the $TE_0$ mode.

5. The method of claim 1, wherein said step of detecting the change of intensity of the evanescent field is performed on the side of the optical guide opposite the side on which the at least one region of the first surface is located.

6. The method of claim 1, wherein said step of detecting the change of intensity of the evanescent field is performed on the same side of the optical guide as the at least one region of the first surface is located.

7. The method of claim 6, wherein said step of detecting the change of intensity of the evanescent field is performed on the same side of said optical guide as the at least one region of the first surface of said optical guide is located and separated therefrom by the analyte.

8. The method of claim 1, wherein the analyte is dissolved in a solvent.

9. The method of claim 1, wherein at least one probe species is immobilized on the at least one region of the first surface of the optical guide, and the analyte contains target species capable of binding to the at least one probe species.

10. The method of claim 1, wherein the optical guide further comprises a second surface opposite the first surface thereof, and wherein a cladding layer is disposed substantially contiguous with the second surface.

* * * * *